(12) United States Patent
Wang et al.

(10) Patent No.: US 11,324,491 B2
(45) Date of Patent: May 10, 2022

(54) CLICK AND RELEASE ENDOBRONCHIAL SPECIMEN COLLECTION HISTOLOGY NEEDLE

(71) Applicant: Ko Pen Wang, Butler, MD (US)

(72) Inventors: Ko Pen Wang, Butler, MD (US); Christopher Britton Lee, Saint Louis, MO (US)

(*) Notice: Subject to any disclaimer, the term of this patent is extended or adjusted under 35 U.S.C. 154(b) by 1183 days.

(21) Appl. No.: 15/600,401

(22) Filed: May 19, 2017

(65) Prior Publication Data

US 2018/0333149 A1 Nov. 22, 2018

(51) Int. Cl.
| | | |
|---|---|---|
| *A61B 10/04* | (2006.01) | |
| *A61B 10/00* | (2006.01) | |
| *A61B 10/02* | (2006.01) | |
| *A61B 1/267* | (2006.01) | |
| *A61B 1/00* | (2006.01) | |

(52) U.S. Cl.
CPC .......... *A61B 10/04* (2013.01); *A61B 1/00131* (2013.01); *A61B 1/2676* (2013.01); *A61B 10/0045* (2013.01); *A61B 10/0283* (2013.01); *A61B 2010/045* (2013.01)

(58) Field of Classification Search
CPC . A61B 10/04; A61B 10/0283; A61B 10/0233; A61B 2010/045; A61B 2010/0208
See application file for complete search history.

(56) References Cited

U.S. PATENT DOCUMENTS

| | | | | |
|---|---|---|---|---|
| 4,817,631 | A * | 4/1989 | Schnepp-Pesch | A61B 10/0283 600/562 |
| 4,907,599 | A * | 3/1990 | Taylor | A61B 10/0275 600/567 |
| 5,246,011 | A * | 9/1993 | Caillouette | A61B 10/0283 600/566 |
| 2004/0019297 | A1* | 1/2004 | Angel | A61B 10/04 600/564 |
| 2005/0090763 | A1* | 4/2005 | Wang | A61B 10/04 600/564 |
| 2011/0190662 | A1* | 8/2011 | McWeeney | A61B 10/04 600/567 |

* cited by examiner

*Primary Examiner* — David J. McCrosky
(74) *Attorney, Agent, or Firm* — Davidson Berquist Jackson & Gowdey LLP (57) ABSTRACT

A controller for use with a hollow endoscopic needle for collecting tissue, cell and/or fluid specimens from a patient that includes an outer body enclosing a slidably retaining a spring loaded plunger, a click and release plunger holder, a vacuum port, and a hollow needle attached to the plunger that is slidably retained in an outer tube or sheath. The controller permits a surgeon to positively control the needle and penetrate tissue, to pulse the needle, and to quickly and positively return the plunger and its needle back to its original un-pushed position. A vacuum or fluid pathway is defined between proximal and distal seals and along the needle's exterior and the interior of the outer tube or sheath and leads to a distal end of the hollow needle. A stylet can be slidably retained within the hollow needle, and can include a sensor to permit navigation.

18 Claims, 10 Drawing Sheets

CLICK AND RELEASE ENDOBRONCHIAL SPECIMEN COLLECTION HISTOLOGY NEEDLE

COPYRIGHT NOTICE

A portion of the disclosure of this patent document contains material which is or may be subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

CROSS-REFERENCE TO CO-PENDING APPLICATIONS

The present invention is related to the following U.S. patents which are all commonly owned with the present application, the entire contents of each being hereby incorporated herein by reference thereto: (1) U.S. Pat. No. 4,532,935, entitled "Bronchoscopic Needle Assembly," Issued on Aug. 6, 1985; (2) U.S. Pat. No. 4,617,940, entitled "Bronchoscopic Needle Assembly," Issued on Oct. 21, 1986; (3) U.S. Pat. No. 4,702,260, entitled "Flexible Bronchoscopic Needle Assembly," Issued on Oct. 27, 1987; (4) U.S. Pat. No. 4,766,906, entitled "Bronchoscopic Needle Assembly," Issued on Aug. 30, 1988; (5) U.S. Pat. No. 4,791,937, entitled "Transendoscopic Needle," Issued on Dec. 20, 1988; (6) U.S. Pat. No. 4,799,494, entitled "Percutaneous Aspiration Lung Biopsy Needle Assembly," Issued on Jan. 24, 1989; (7) U.S. Pat. No. 4,890,626, entitled "Removable Locking Device For Use With Syringes," Issued on Jan. 2, 1990; (8) U.S. Pat. No. 4,966,162, entitled "Flexible Endoscope Assembly," Issued on Oct. 30, 1990; (9) U.S. Pat. No. 5,320,110, entitled "Pleural Biopsy Syringe-Needles," Issued on Jun. 14, 1994; (10) U.S. Pat. No. 7,147,607, entitled "Transendoscopic Double Needle Assembly," Issued on Dec. 12, 2006; (11) U.S. Pat. No. 7,204,812, entitled "Transendoscopic Needle Assembly," Issued on Apr. 17, 2007; and (12) U.S. Pat. No. 9,295,454, entitled Double Lumen Or Double Wire Endobronchial Ultra-Sound Guided Histology Needle (EBUS), issued on Mar. 29, 2016.

FIELD OF THE DISCLOSURE

This disclosure relates generally to an endobronchial ultrasound guided cytology/histology needle assembly for use with a flexible bronchoscope, endoscope or any other type of body cavity scope, and to biopsy devices, and in particular, to needle biopsy devices for collecting tissue, fluid and/or cell samples in conjunction with endobronchial ultra sound (EBUS) procedures, in which an interior of a hollow specimen collection needle is connected to a vacuum source and is movable within an outer hollow catheter.

BACKGROUND OF THE INVENTION

EBUS procedures have been used for many years and allow thoracic surgeons and physicians to use a bronchoscope or endoscope to be inserted and guided through a patient's mouth and trachea and with the scope fitted with an ultrasound processor and a fine gauge aspiration needle is guided through a portion of the scope. Once appropriately positioned, the needle portion of the fine needle aspiration device is advanced into a lymph node or other lesion, the sample is aspirated and the device is removed from the bronchoscope. Such devices pay an increasingly important part in the role of diagnosis and staging of thoracic malignancies.

The foregoing Wang patents relate to this same inventor's approaches in designing completely flexible bronchoscopic needle assemblies that permit relatively non-invasive biopsy procedures to be performed utilizing such needles in combination with, for example, a fiber optic bronchoscope.

The attending physician inserts the bronchoscope into a predetermined one of the patient's natural orifices depending upon the particular organ desired to be biopsied. The needle assembly, which in this invention includes an outer catheter and an inner hollow needle, is slidably inserted into a receiving passageway of the bronchoscope.

Further, the needle assembly can also employ a stylet slidably received within the hollow needle, and the end of the stylet can be provided with an electromagnetic tip to aid in and permit the tip of the needle assembly to be correctly navigated to a chosen site within a patient. There the distal end of the needle assembly can be urged against tissue, for example the lung's interior wall, and when the needle is pushed out of the needle assembly it would pass into the tissue of the patient, and by using a stabbing force exerted through use of the controller the distal end of the needle will penetrate tissue and a sample can be obtained. The bronchoscope enables the attending physician to accurately position the needle and to penetrate the exact location of the desired organ due to the viewing capabilities provided thereby.

SUMMARY OF THE INVENTION

The present invention provides a flexible, endobronchial, ultrasound or otherwise guided or unguided, cytology/histology needle assembly that can be used in a standard bronchoscope or endoscope for obtaining biopsy samples. Such needles have been used for some time and control over their use has sometimes been an issue for the surgeon.

The present invention concerns a novel proximal end controller for these needle assemblies that not only provides a very positive way of handling the needles, but by using the click and release mechanism the controller allows very positive yet simple control over the needle, and most importantly the ability to control needle extension and retraction as well as the ability to pulse the needle into and out of tissue to be sampled, thereby easing tissue and/or fluid specimen collection. The needle assembly is easily maneuvered through a scope to a chosen site within a patient, and the needle can also be provided with suitable navigational devices, and the needle is easily telescopically extended and inserted into the patient's target tissue.

In one embodiment, the present invention is directed to a controller for moving and controlling a hollow needle of a medical specimen collection device which includes an outer sheath in which a flexible hollow needle is slidably mounted thereby providing a specimen collection capability at a distal end of the needle. A flexible stylet, also having proximal and distal ends, can be slidably and coaxially received within the hollow needle, with its proximal end directly connected to a cap at one end of a needle controlling plunger provided within the controller, and with it is distal end adjacent the needle's distal end.

In a second embodiment the stylet can be provided with a tip using an electro magnetic portion to permit the device to be navigated for example by using techniques as, for example, are discussed in U.S. Pat. No. 8,696,549 and others owned by Veran Medical Technologies, Inc. of St. Louis Mo., which is hereby incorporated herein in its entirety by reference thereto. It is not believed that further discussion of navigational techniques is required for a complete understanding of such techniques. In another embodiment the stylet can be omitted and the needle would be used by itself.

In each embodiment the syringe preferably provides a source of vacuum directly into the collection needle, but other vacuum sources can be used.

Glossary: As used throughout this document:

The phrase "EBUS needle" shall mean a flexible endobronchial ultrasound guided transbronchial needle assembly.

The term "leur lock or leur lok" shall include any tapered fitting that is a standardized system used on medical devices for small-scale fluid fittings, and are typically used for making leak-free connections between a male-tapered fitting and its mating female part on medical instruments, such as syringes. Luer-Lok™ type fittings are securely joined by means of a tabbed hub on the female fitting which screws into threads in a sleeve on the male fitting.

The term "outer tubular sheath" shall refer to an outer cover or tubular structure that is fixed to the controller and extends along the length of a hollow needle and through which that needle can slidably move. The outer tubular sheath is preferably formed from a clear, flexible material with an interior that is connected to a vacuum port to thereby establish a vacuum pathway.

The term "vacuum pathway" refers to a fluid channel or space defined between an exterior of the hollow needle and the interior of the outer tube, with proximal and distal ends defined between spaced apart seal members, and which is operatively connected to a vacuum source and leads to a distal end of the hollow needle through an opening provided adjacent the needle's distal end that is normally closed by a stylet.

DESCRIPTION OF PRESENTLY PREFERRED EXAMPLES OF THE INVENTION

Brief Description of Figures

The invention is better understood by reading the following detailed description with reference to the accompanying drawings in which.

DETAILED DESCRIPTION

A. Overview

To gain a better understanding of the invention, a preferred embodiment will now be described in detail. Frequent reference will be made to the drawings. Reference numerals or letters will be used throughout to indicate certain parts or locations in the drawings. The same reference numerals or letters will be used to indicate the same parts and locations throughout the drawings, unless otherwise indicated.

B. Environment

The preferred embodiment now described will be with respect to use with a standard bronchoscope and the procedures used when collecting one or more tissue, cell and/or fluid specimens from a patient. The scale of the embodiment, therefore, is to be understood with respect to this type of article. It is to be understood as well, however, that the invention is applicable to other articles and its scale can vary accordingly.

C. Structure

Figure 1:
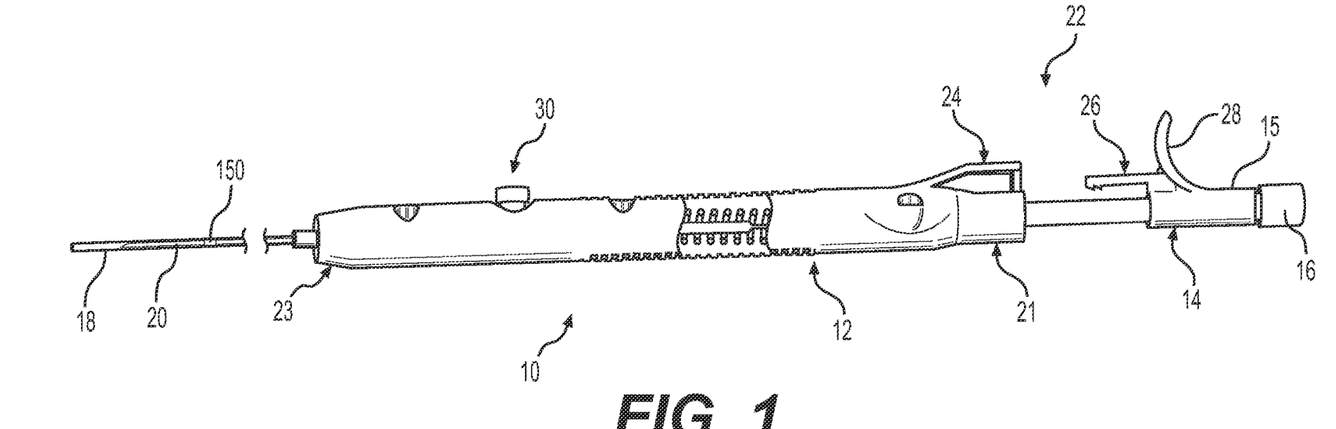
FIG. 1 is a elevational view of an endoscope/bronchoscope needle and a click and release controller with a needle control a plunger in a fully retracted position with a portion cut away to show an uncompressed spring.
Figure 3:
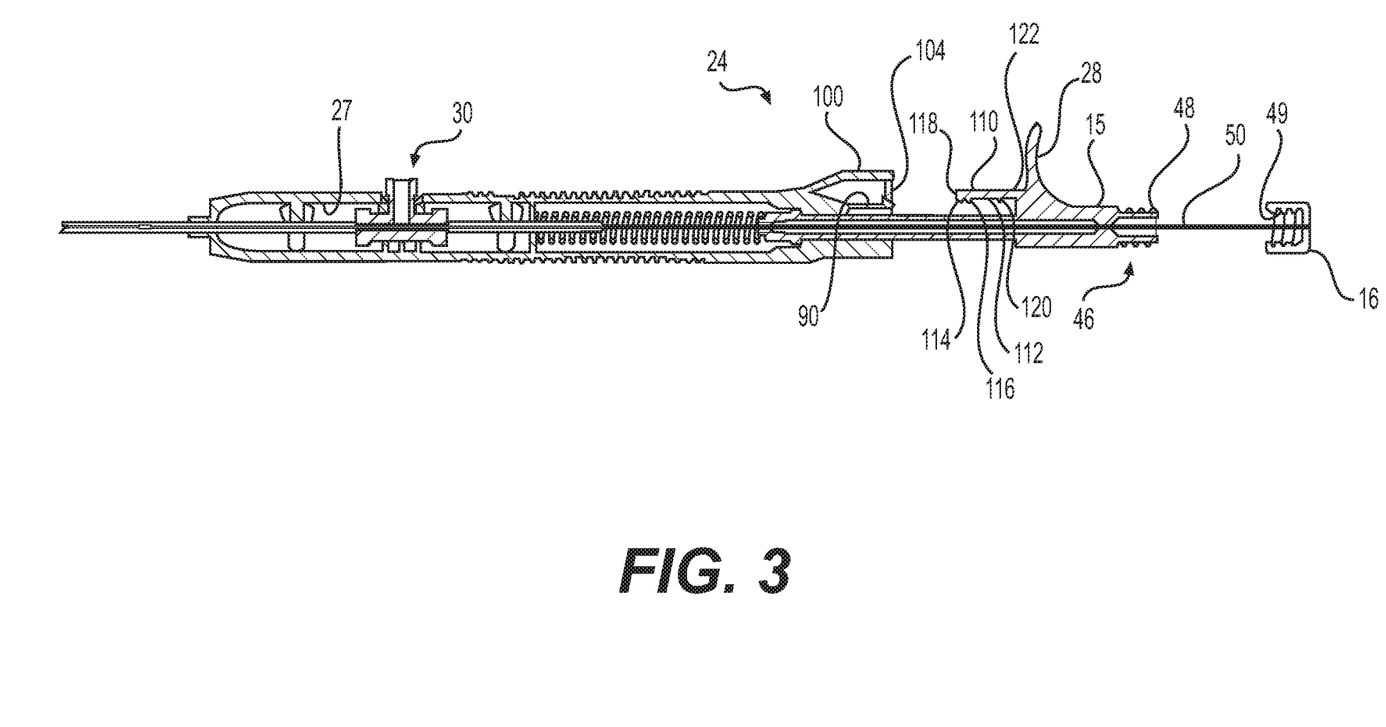
FIG. 3 shows a cross sectional view of the controller of FIG. 1 with an end cap disconnected and pulled away along with an attached stylet.
Figure 6A:
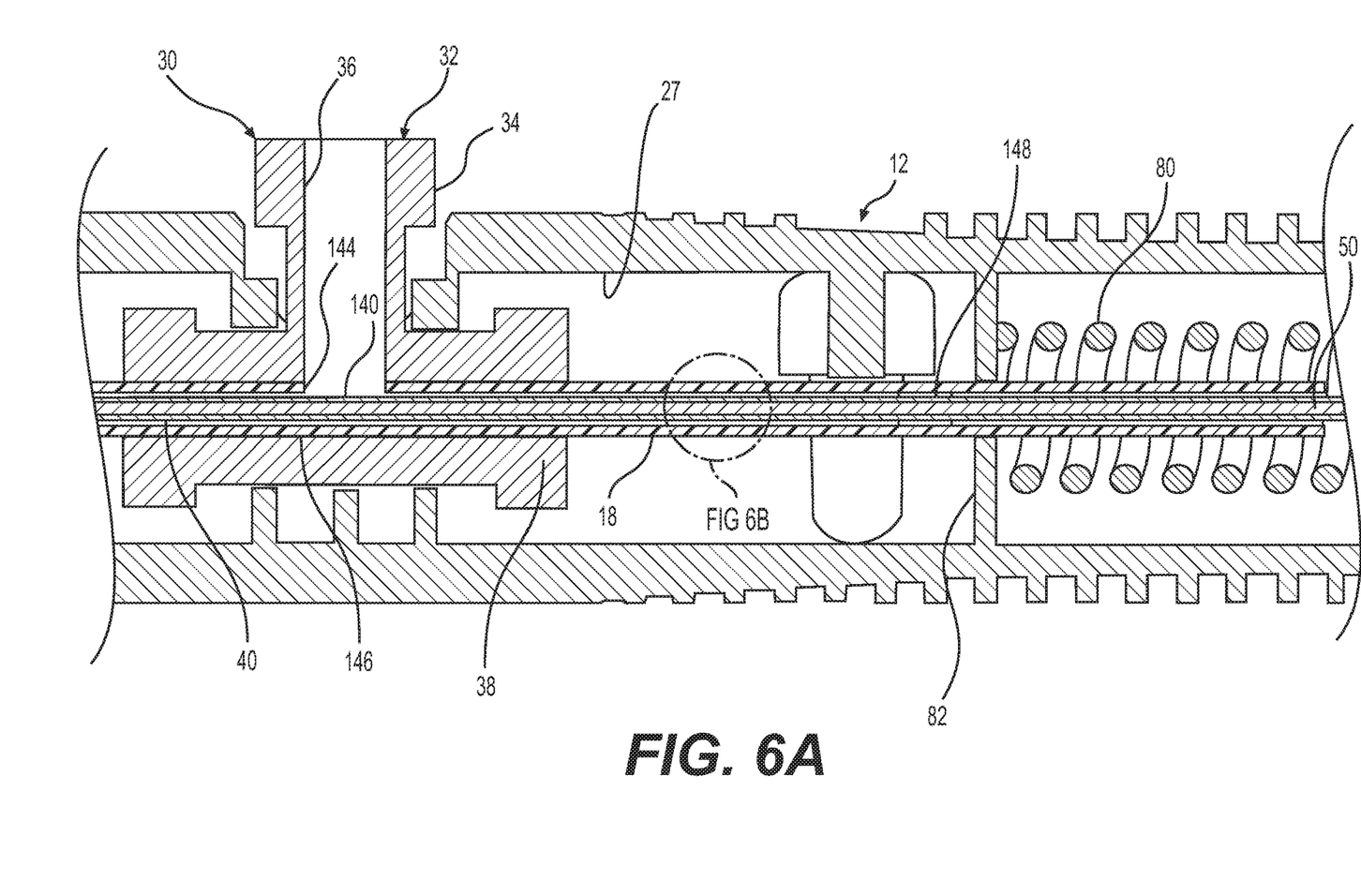
FIG. 6A is an enlarged cross sectional view of a portion of the controller showing a vacuum port and parts within the controller.

FIG. 1 shows a single use aspiration needle controller 10 that includes an outer body 12, a plunger 14 with a hollow interior slidably mounted within the body 12, a cap 16 closing a hollow proximal end of the plunger 14 an outer heath 18 that is connected within the outer body 12 and a hollow needle 20 that is connected to the plunger 14. The outer body 12 has a proximal end 21 and a distal end 23, and a hollow interior 27 as shown in FIGS. 3 and 6, for example. The controller 10 also includes a click and release mechanism 22 adjacent the proximal end 21 comprised of a female portion 24 that is formed as a part of the proximal end 21 of the outer body 12 and a male portion 26 that is formed as a part of the proximal end 15 of plunger 14. The plunger 14 also includes a handle 28. While plunger 14 is preferably provided with a hollow interior along its length, to permit a stylet 50 to pass there through, where no stylet is to be used the plunger 14 could be a solid structure without a hollow interior.

The outer body 12 and the plunger can be made from any plastic material, thermoplastics, or other moldable materials. The body 12 is preferably molded on two halves that can be connected together around the plunger, the vacuum port 30, the needle and outer sheath 18, and the spring 80 by being screwed together, by use of screws or other mechanical techniques, adhesives, epoxies, by welding techniques, or other bonding approaches. The outer tube or sheath is preferably made from PTFE or a similar material.

The needle 20 is preferably a 21 gauge and made from nitinol, while the stylet 50, slidingly mounted within needle 20, can have, for example, a 0.0220" outer diameter, and can also be made from nitinol. It should be understood that other gauge needles and stylets can be used and they can be made form the same materials or different materials, which can include stainless steel and other similar materials used for needles and stylets.

The controller 10 also includes a vacuum or "T" port 30, as shown in detail in FIG. 6A, that has an outer end 32 formed with a Leur-Lok connection, which can be located at a mid-point along the length of controller 10. A vertically extending portion 34 includes an internal bore 36 that leads to and opens into a horizontal bore 40 formed in a horizontal portion 38. The vacuum port 30 is bonded or otherwise mechanically attached to and within the outer body 12 so that the outer end 32 extends outwardly beyond the outer surface of the controller outer body 12 and so that the horizontal bore 40 is centered within controller 10 and aligns with a hollow bore 42 within plunger 14. This vacuum or T port 30 is a separate structure from the body 12 and can be mechanically retained within the outer body or can be bonded or held in place by a suitable adhesive. This port 30 can also be made from any thermoplastic, nylon, plastic or other similar material.

Figure 5:
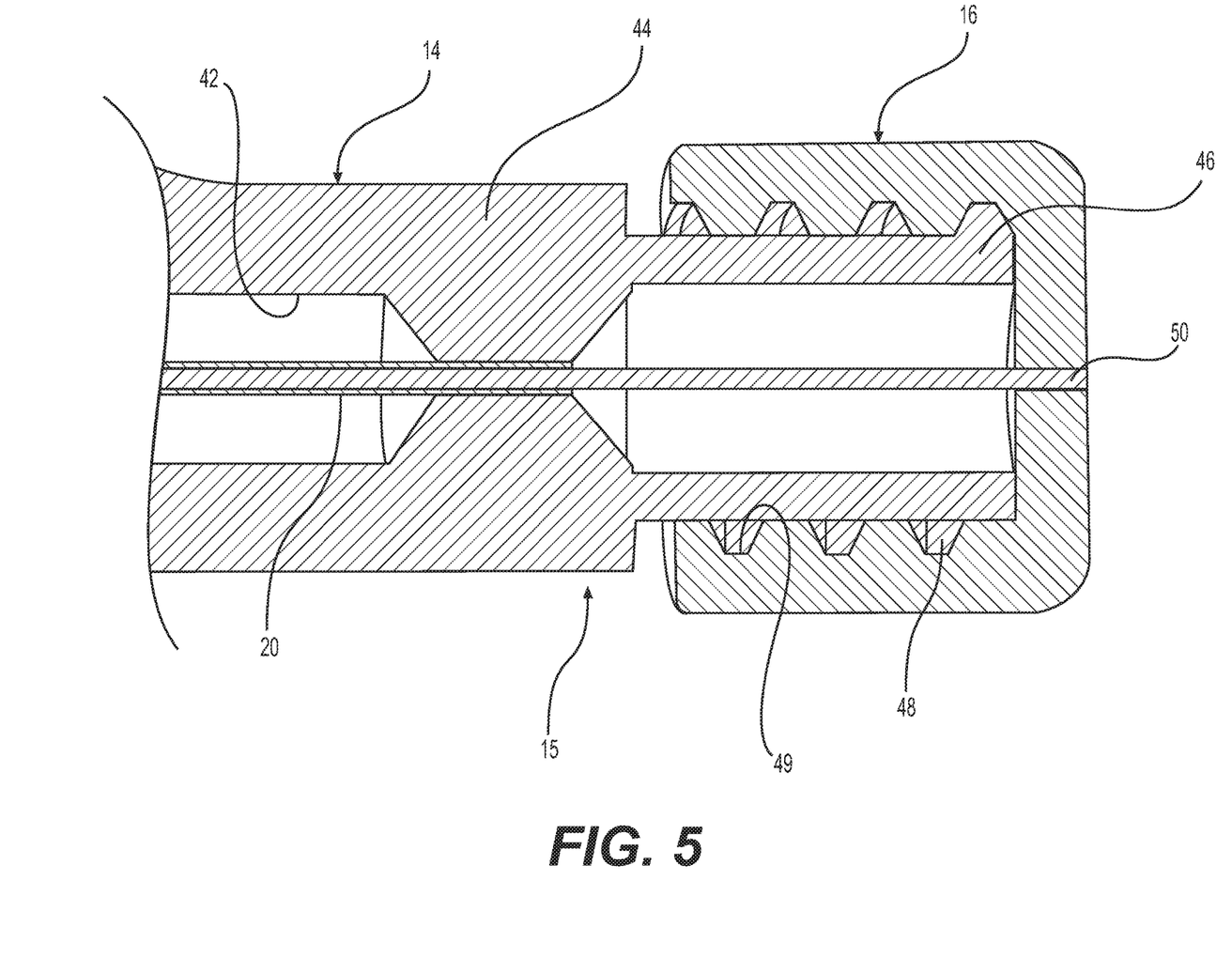
FIG. 5 shows a detailed cross sectional view of the cap end of the plunger and the needle bonding point.

FIG. 5 shows that the needle 20 as being fixed centrally within the outer body 12 and to an inwardly projecting cylinder 44 provided within the hollow bore 42 of plunger 14 adjacent the proximal end 15. The proximal end 15 of plunger 14 also includes a hollow cylinder 46 located proximally of cylinder 44 that has a threaded exterior 48 to mate with a threaded interior 49 of cap 16. That threaded connection 48/49 could instead be formed as a Leur-Lok type connector structure to be able to mate with any device having Leur-Lok mating connection.

Figure 4A:
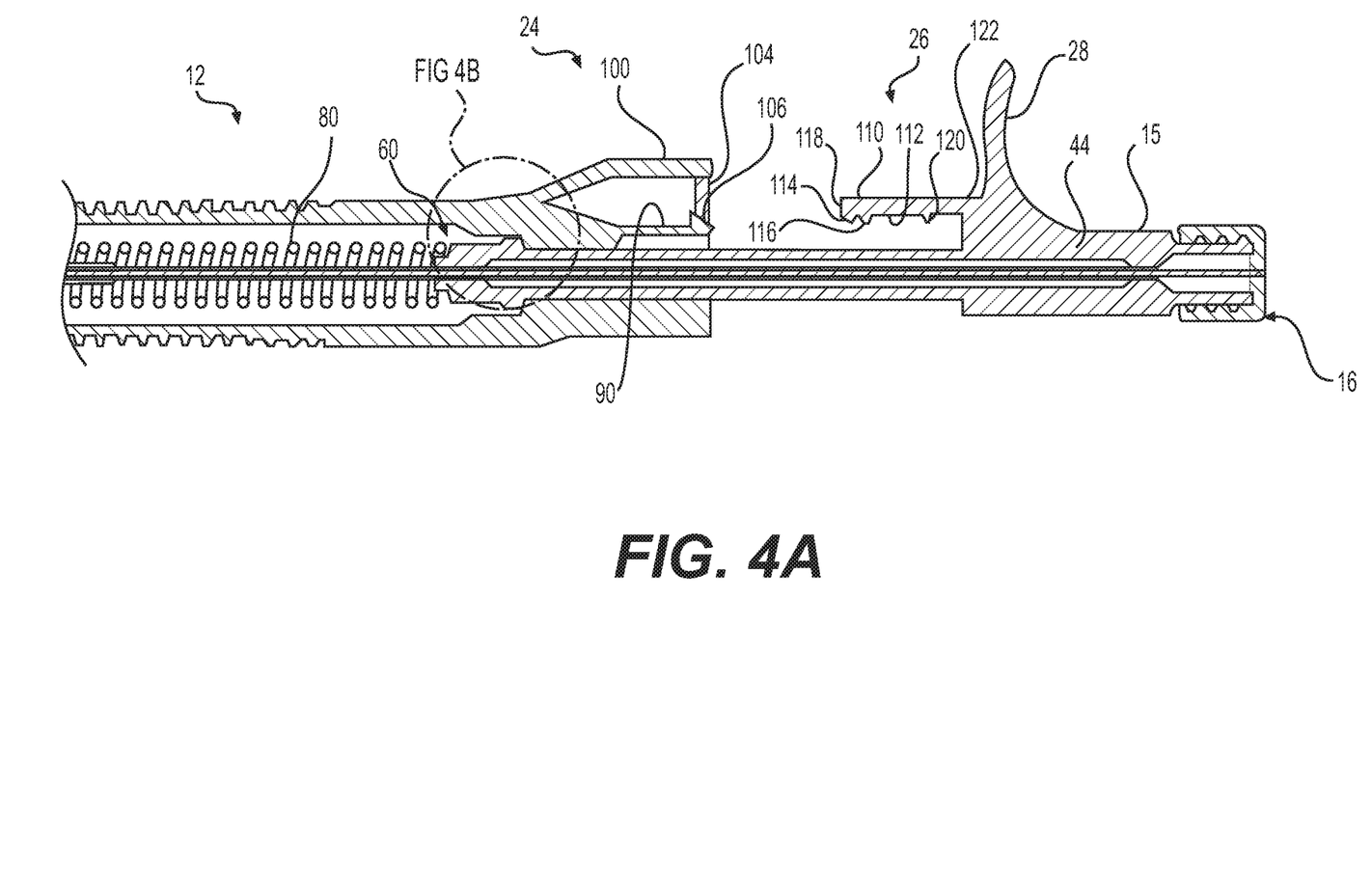
FIG. 4A shows an enlarged cross sectional view with the proximal end of the controller.
Figure 7:
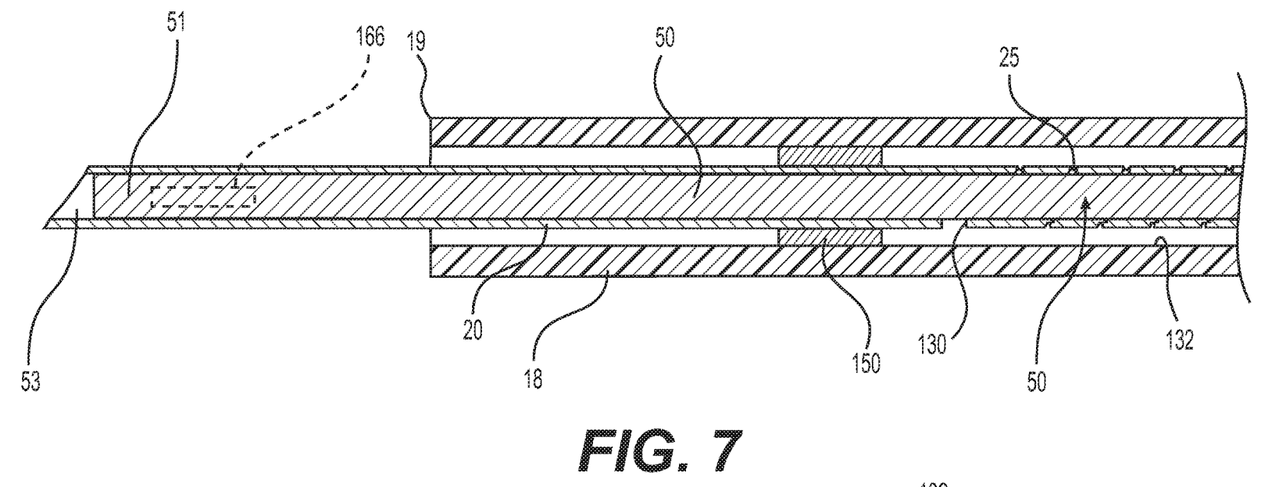
FIG. 7 is an enlarged view of the distal end of the needle and outer sheath with the needle housed within the outer sheath.
Figure 8:
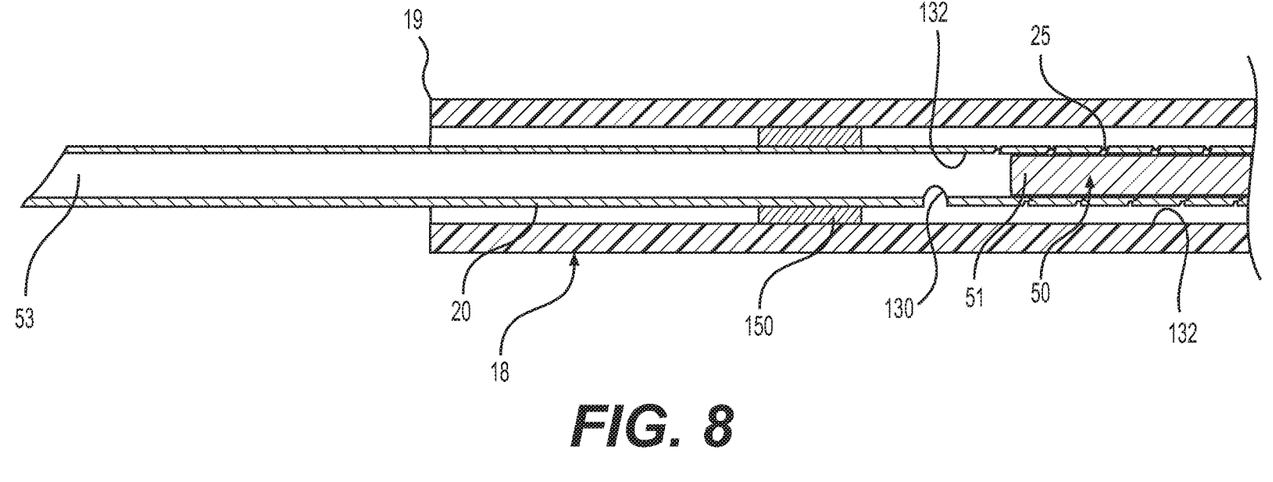
FIG. 8 is an enlarged view of the distal end of the needle and outer sheath with the needle extended beyond the outer sheath.

Cap 16 is also shown in FIGS. 4 and 5 as having a stylet 50 fixed to a central part of cap 16 and as being slidably mated into hollow needle 20 and extending toward the distal end 53 of needle 20, as shown in FIGS. 7 and 8, for example. When cap 16 is connected to the threads 48 on plunger 14 the distal end 51 of the stylet 50 will extend almost to the full length of hollow needle 20 as shown in FIG. 7. When the cap 16 is disconnected from the proximal end of plunger 14 and pulled away this slides stylet 50 proximally inwardly from the distal end 53 of needle 20 as shown in FIG. 8.

Figure 4B:
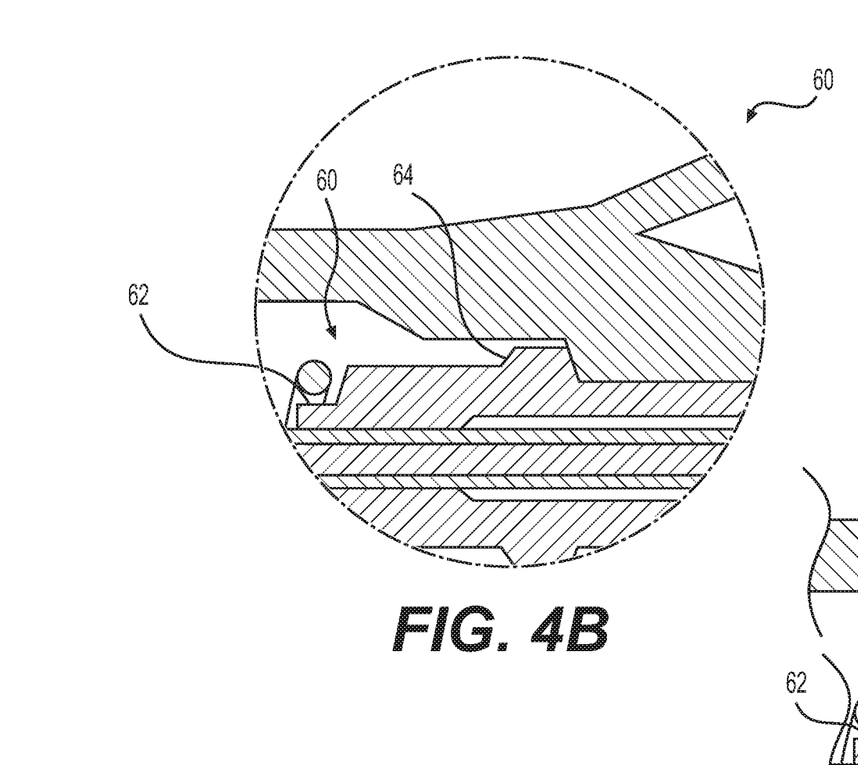
FIG. 4B is an enlarged cross sectional view of a portion of FIG. 4A showing the plunger stop.
Figure 4C:
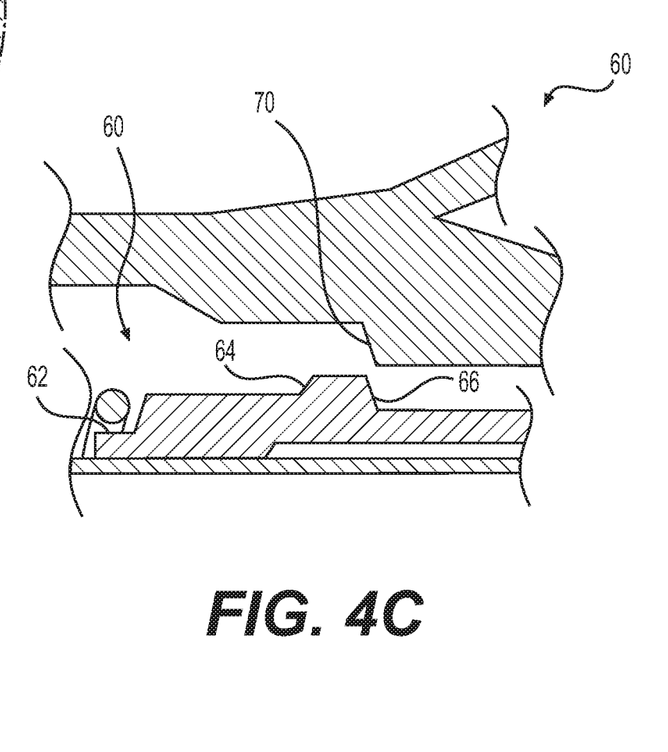
FIG. 4C is an enlarged cross sectional view of FIG. 4B with portions separated for clarity.

In FIG. 4A there is an enlarged view of the proximal portion of controller 10 and, along with FIGS. 4B and 4C, shows plunger 14 as having a distal end 60 that includes a reduced cylinder portion 62 and a raised circular stop 64, located proximally from the cylinder portion 62, that includes a proximally facing wall 66. A portion of the hollow interior 27 of the outer body 12 is formed with a circular wall 70, spaced inwardly or distally from the proximal end 21 of the outer body 12, which is sized to mate with wall 66 to act as a stop for plunger 14 when walls 66 and 70 interconnect. Also included within controller 10 is a spring 80 that will fit onto the reduced cylinder portion 62 and extend to a circular wall 82 located within the hollow interior 27 of outer body 12 and spaced distally from wall 70. Spring 80 is preferably made from metal, but could be formed from other materials so long as its spring force is sufficient to move the plunger 14 proximally when the plunger is released. When the plunger 14 and spring 80 are both in place within controller 10 the spring 80 will be slightly compressed between the distal end 60 of plunger 14 and the circular wall 82 as is shown in the cut away portion of in FIG. 1. As plunger is thereafter progressively pushed into the outer body 12 spring 80 will be progressively compressed, as is shown in the cut away portion of FIG. 2, and when the click and release mechanism is released spring 80 will urge plunge 14 outwardly or proximally until stopped by the mating walls 66 and 70.

Figure 9:
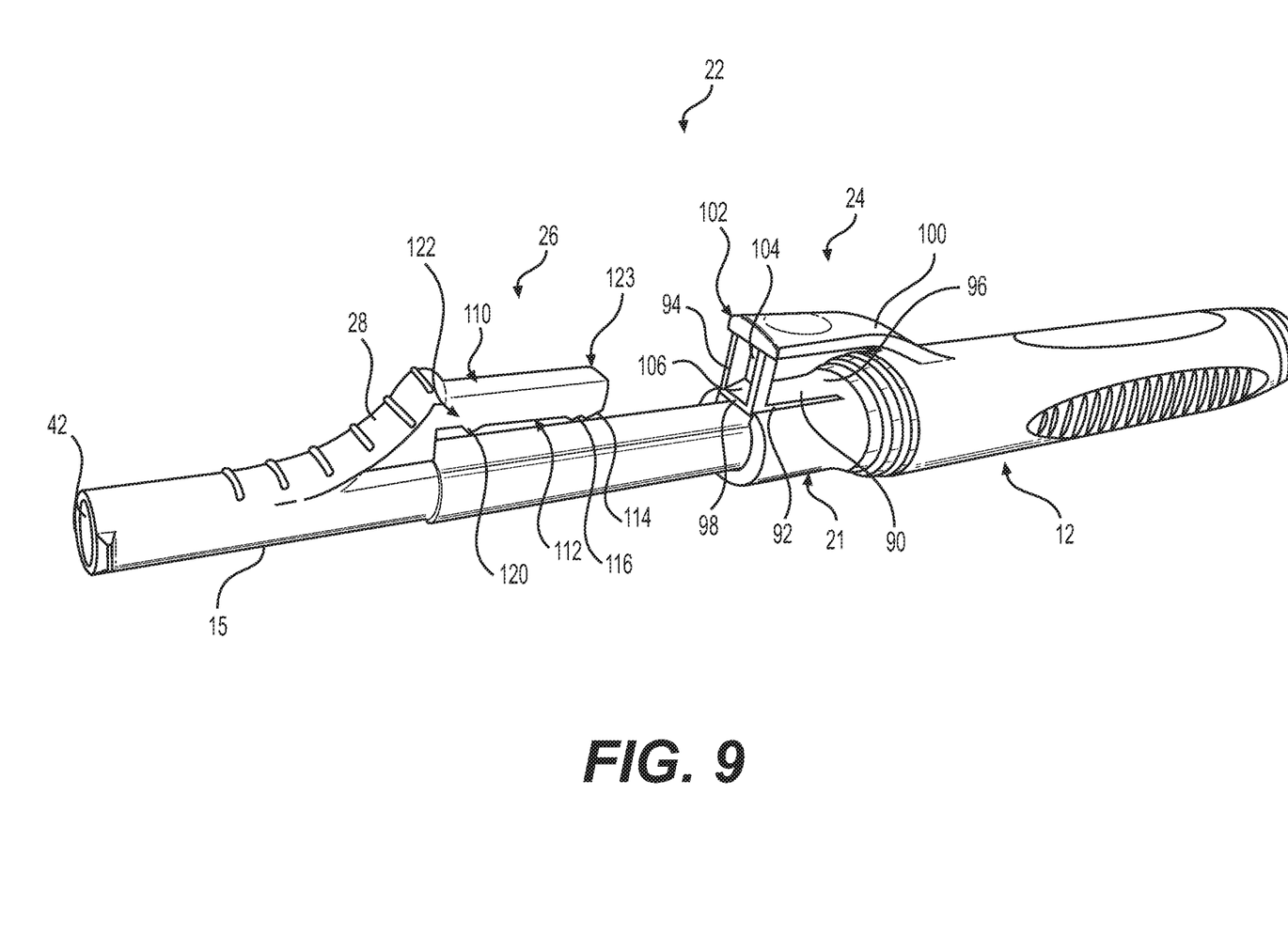
FIG. 9 shows an enlarged perspective view of the click and release mechanism.

The click and release mechanism 22 is best shown in FIG. 9 as being comprised of two portions, as noted above, with the female portion 24 being formed at the proximal end 21 of the outer body 12 and the male portion 26 located adjacent the proximal end 15 of plunger 14. The female portion 24 includes a flexing wall portion 90 having two sides 92 and 94 that are each spaced from outer body 12, a bottom connecting wall 96, and a proximal end 98. A handle 100 extends outwardly from the outer body 12 from a point just distally of the connecting wall 96 and has an L-shaped portion with a proximal portion 102 that connects to the flexing wall portion 90 adjacent a proximal end 98 of all portion 90. The proximal end 102 of handle 100 is formed with a shaped opening 104 that includes a catch or pawl 106. Opening 104 preferably rectangular in shape.

The male portion 26 of the click and release mechanism 22 includes a projection 110 that extends distally away from handle 28 parallel to and spaced from plunger 14 and has a proximal end 122 and a distal end 123 having a front surface 118. The portion 26 preferably has a substantially square cross section and includes a wall 112 facing plunger 14. Wall 112 can be provided with at least one tooth or locking lug 114, and more preferably two lugs or teeth 114 and 116 adjacent the distal end 123 of projection 110, and another tooth or locking lug 120 adjacent a proximal end 122 of projection 110. Teeth 116 and 120 are separated by a gap or span along wall 112 that permits a user to pulse the plunger 14 back and forth in along that gap portion thereby pulsing needle 20 repeatedly back and forth or in and out of the area of the tissue being sampled by the combined effects of spring 80 and the user pushing on handle 28.

Flexible wall portion 90 is normally in an unflexed condition lying substantially parallel with the outer body 12. The handle 100 of the click and release mechanism connects between the outer body 12 and the proximal end 98 of the flexible wall portion 90 so that by pushing handle 100 inwardly likewise pushes the wall portion 90 inwardly. In its unflexed condition the pawl 106 will be engaged by one of the teeth 114, 116 and/or 120 and will thereby retain the plunger 14 in a plunged or inwardly pushed position corresponding to which tooth is retained by pawl or catch 106 as the distal end 123 of projection 110 is pushed through opening 104. When handle 100 is pushed inwardly pawl 106 will be released from its holding position of one of the teeth 114, 116 or 120 and the formerly retained tooth will be released and spring 80 will push projection 110 out of the opening 104 and thereby plunger 14 proximally out of the outer body 12.

As plunger 14 is pushed inwardly or distally against the force of spring 80 both needle 20 and stylet 50, if present, will be pushed distally thereby sliding the needle distal end 53 toward and beyond the distal end 19 of the outer tube or sheath 18 as is shown in FIG. 7. To create a vacuum at the needle distal end 51 the stylet 50 can be slid proximally by disengaging cap 16 from the proximal end 46 of plunger 14 to slide the stylet 50 proximally beyond an opening 130 thereby opening a vacuum pathway into hollow needle 20 and to its distal end 53 as is shown in FIG. 8. It should be understood that there will preferably be a relatively tight fit between the stylet 50 and the interior of hollow needle 20 so as to assist in maintaining any applied vacuum within a vacuum pathway 132. The hollow needle 20 can also be provided, if it is desired to make it more flexible, with a scored, serrated, or shaped exterior, as shown at 25 in FIGS. 7 and 8, that will make the needle more flexible and bendable within the endoscope apparatus.

Figure 2:
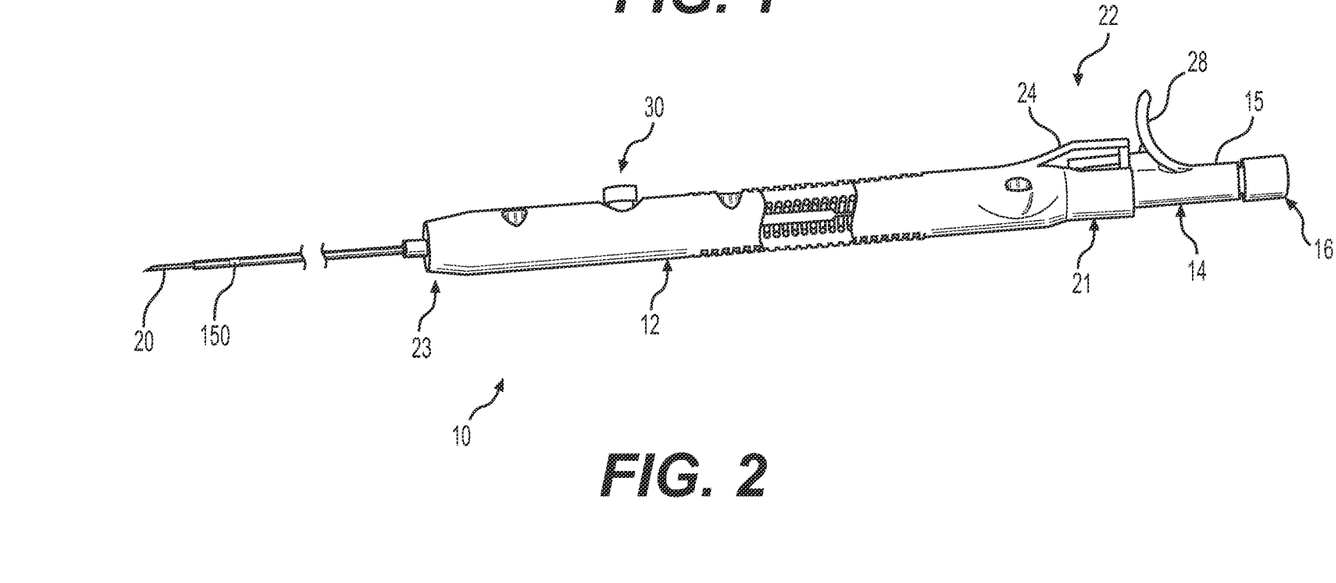
FIG. 2 is similar to FIG. 1 but shows the plunger in a fully engaged position and a cut away portion showing the spring compressed.
Figure 6B:
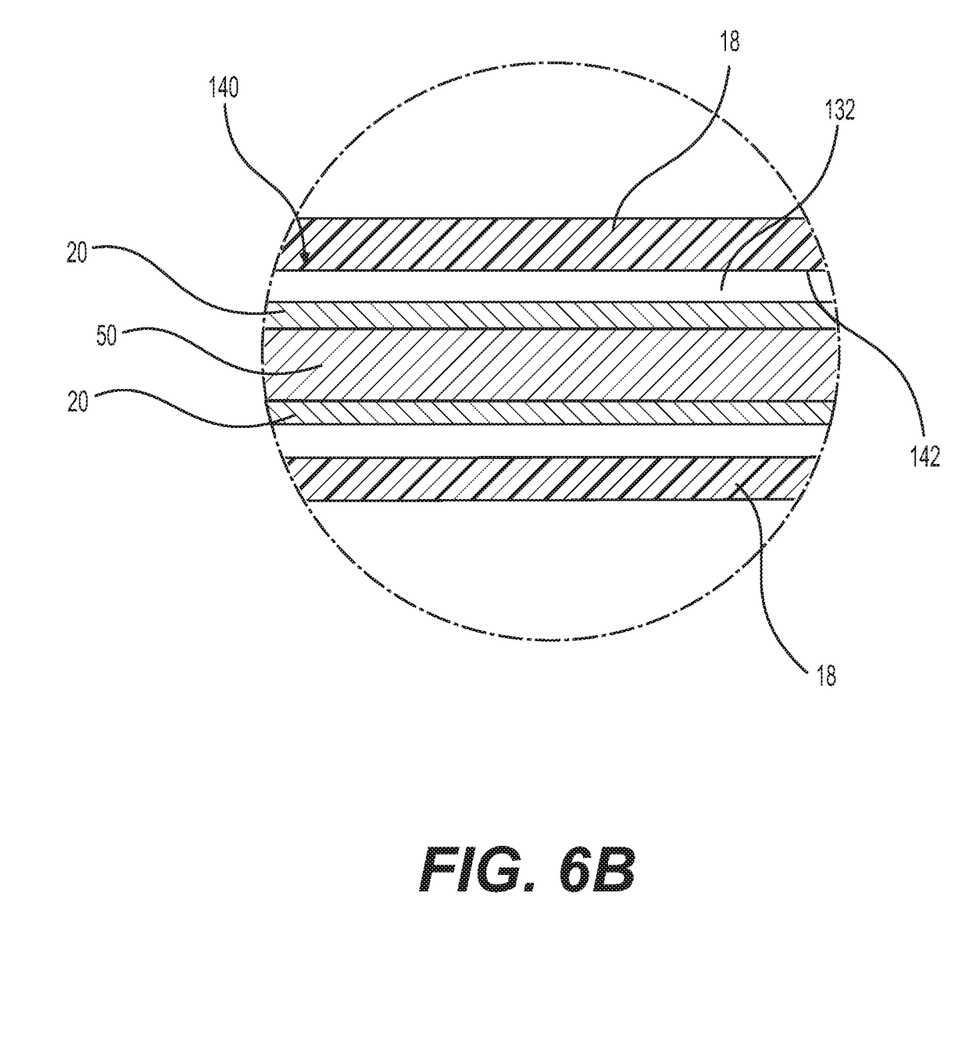
FIG. 6B shows an enlarged view of a portion of FIG. 6A and the relationships between the outer sheath, the hollow needle and the stylet.

The vacuum path 132 is developed initially within the vacuum or T port 30 and preferably extends along the space between an exterior surface 140 of needle 20 and an inner surface 142 of the outer tube or sheath 18 as is shown in FIG. 6A and in greater detail in FIG. 6B. That outer tube or sheath 18 is preferably fixed within the controller 10 by being bonded, glued, welded or otherwise fixed within bore 40 of the vacuum or T port 30, or alternatively within the circular wall 82, or at some other point within the interior of the outer body 12. It should be understood that to create the fluid or vacuum path 132 a portion of the outer tube or sheath 10 will be cut away, as shown at 144, from an upper portion thereof where the outer tube or sheath 18 is in registration with the vertical bore 36, while the remainder of the outer tube or sheath 18 will remain intact around the remainder of bore 40 as is shown at 146. The needle's exterior 140 will then be exposed within that cut out 144 and be directly connected to the bore 36. Further, a seal 148 is provided on needle 20 at a location proximally of the vacuum port 30 and preferably adjacent wall 82 when plunger 14 is in it's released condition, and will still be proximal of the vacuum port 30 when the plunger 14 is fully pushed inwardly or distally along its sliding path. A second seal 150, shown in FIGS. 7 and 8, is provided distally of the cut out 130 on needle 20 near distal end 21, but proximally of that distal end 21. At that location seal 150 will also be positioned proximally of the outer tube's distal end 19 when the plunger 4 is fully released yet still within the interior of the outer tube or sheath 18 when the plunger 14 is fully pushed inwardly or distally along its sliding path as FIG. 2 shows. The seals 148 and 150 are preferably made from a polyurethane elastomer or another similar material that will be compatible with the needle 20 and the outer sheath 20.

Thus, with bore 36 in fluid contact with the interior 142 of the outer tube or sheath 18 through cut out 144 the fluid or vacuum pathway 132 will be established along the exterior 140 of needle 20, the interior 142 of the outer sheath 18, and between seals 148 and 150.

Figure 10:
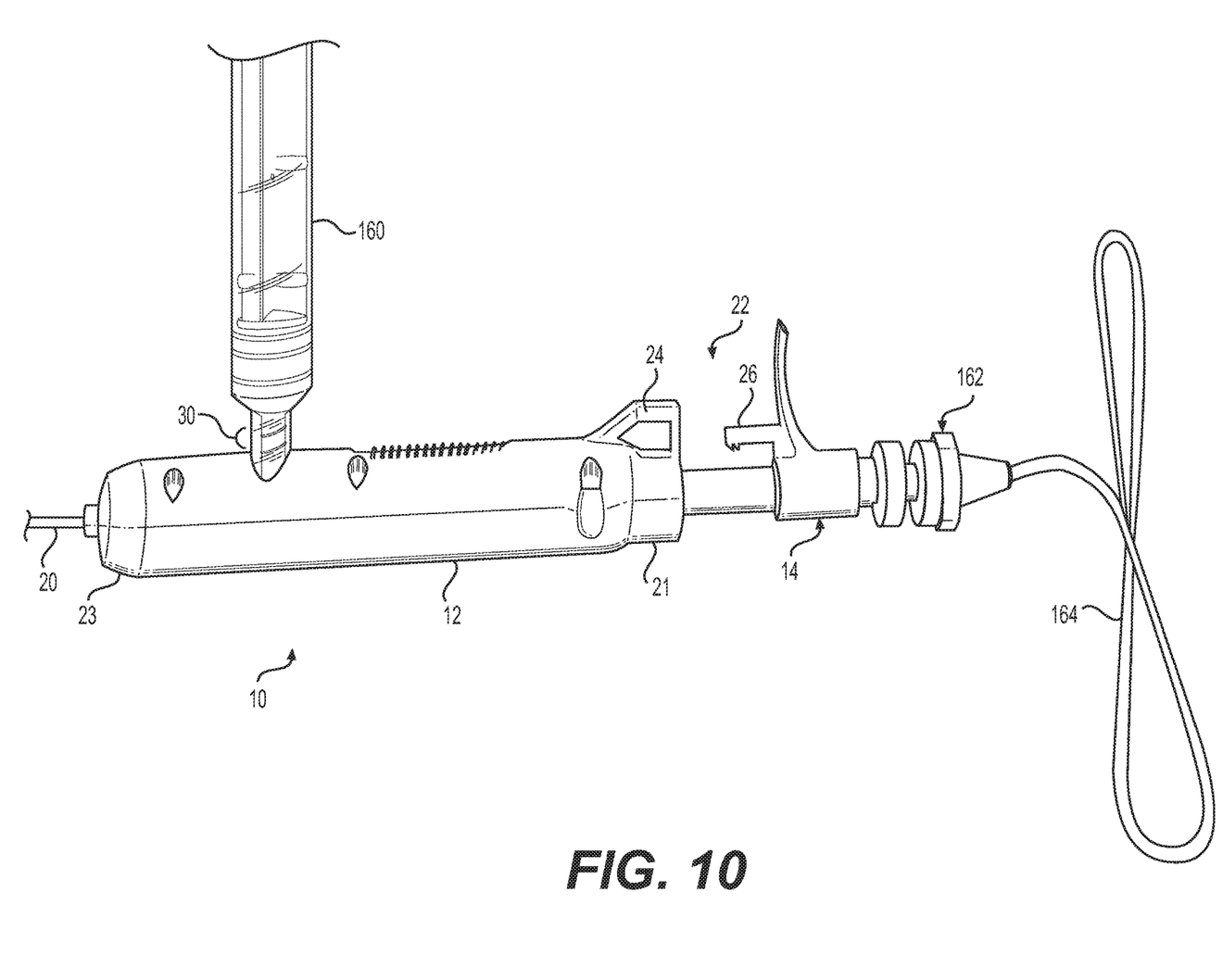
FIG. 10 shows the present invention with an attached navigation and guidance elements and a syringe attached to the controller.

FIG. 10 shows controller 10 with a syringe 160 connected to port 30, and a modified sensor cap 162 that includes an electrical connector 164 to a navigation system as replacing cap 16. The stylet 50 will, in this instance, include an electromagnetic tip, as shown in phantom at 166 in FIG. 7, which will be observable by suitable navigation apparatus as previously discussed herein.

It should be understood that as an alternative construction, where plunger 14 has a hollow interior, the hollow needle 20 would be aligned with that plunger hollow interior, the vacuum port 30 could be closed or eliminated, along with the proximal seal 148, the outer tube 18 could be extended to the plunger's distal end, and the vacuum connection could be provided at the proximal end 15 of plunger 14 to establish a vacuum pathway from the plunger, through the gap between the outer tube and the needle, to the needle's distal end 21.

D. Operation

To use the present invention a surgeon or attending physician will first thread the outer tube or sheath into an endoscope and once the distal end 53 of the needle 20 has been positioned at a desired location handle 28 will be used to push plunger 14 into the outer body 12 to push the needle distal end 53 beyond the outer tube or sheath 18. If present the stylet can then be pulled proximally to open a vacuum pathway onto the hollow needle 20 and its distal end 53 and the plunger can be pushed back and forth along the spaced gap between teeth 116 and 120 to thereby repeatedly push the hollow needle 20 and its distal end 53 into a site to collect tissue, cell and/or fluid specimens with the added assistance of the vacuum supplied via the fluid pathway 132. When this specimen collection process is completed handle 100 can be pushed and needle 20 will be automatically retracted into the outer tube or sheath 18 thereby protecting the collected specimens during the withdrawal of the device from the endoscope.

When introducing elements of various aspects of the present invention or embodiments thereof, the articles "a," "an," "the" and "said" are intended to mean that there are one or more of the elements, unless stated otherwise. The terms "comprising," "including" and "having," and their derivatives, are intended to be open-ended terms that specify the presence of the stated features, elements, components, groups, and/or steps, but do not exclude the presence of other unstated features, elements, components, groups, and/or steps and mean that there may be additional features, elements, components, groups, and/or steps other than those listed. Moreover, the use of "top" and "bottom," "front" and "rear," "above," and "below" and variations thereof and other terms of orientation are made for convenience, but does not require any particular orientation of the components. The terms of degree such as "substantially," "about" and "approximate," and any derivatives, as used herein mean a reasonable amount of deviation of the modified term such that the end result is not significantly changed. For example, these terms can be construed as including a deviation of at least +/−5% of the modified term if this deviation would not negate the meaning of the word it modifies.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A click and release controlled endoscopic needle for collecting tissue, cell and/or fluid specimens from a patient comprising:

a controller comprising an outer body having a hollow interior and proximal and distal ends, an internal stop, a plunger also having a proximal portion for providing control by a surgeon and a distal portion at least a portion of which is slidably received within the outer body, and a spring interposed between the internal stop and a distal end of the distal portion;

the controller including a vacuum connection;

a click and release mechanism operatively interposed between the plunger and the outer body to control the relative sliding positions there between, the click and release mechanism comprising a proximally facing flexible member at the proximal end of the outer body including a pawl, the plunger further including a distally extending projection spaced above and parallel to the distal portion and located at an intermediate position between proximal and distal ends of the plunger, the distally extending projection having a series of spaced apart outwardly projecting teeth formed thereon for releasably engaging the pawl when the projection is moved over the pawl of the flexible member, at least two of the series of teeth being spaced apart defining a smooth surface there between to permit the plunger to be pulsed there along, and a handle member located adjacent the proximal end of the plunger;

a hollow needle having a proximal end attached to the plunger and a distal end for collecting specimens and having an opening therein adjacent the distal end, a flexible outer tube attached to the controller and extending along the length of the needle and operatively connected to said vacuum connection so as to permit a fluid pathway to be established and defined along and between an exterior surface of said hollow needle and an inside surface of said outer tube and through said opening in the hollow needle into the distal end of the hollow needle, and spaced apart fluid seals defining proximal and distal ends of said fluid pathway.

2. The click and release controlled endoscopic needle as in claim 1 wherein the teeth on the distally extending projection are released by moving the flexible member toward the interior of the outer body.

3. The click and release controlled endoscopic needle as in claim 2 wherein the distally extending projection includes at least a portion of said plurality of spaced apart teeth adjacent a distal end of the projection and distally spaced from the smooth surface.

4. The click and release controlled endoscopic needle as in claim 2 wherein the distally extending projection has a length permitting the plunger to be moved distally and proximally against the spring without being locked in place.

5. The click and release controlled endoscopic needle as in claim 1 wherein the fluid seals comprise a first fluid seal positioned on said hollow needle proximately of said vacuum connection to define a proximal end of said fluid pathway, and a second fluid seal positioned on said hollow needle between the needle distal end and the opening to define a distal end of said fluid pathway.

6. The click and release controlled endoscopic needle as in claim 1 wherein the vacuum connection is positioned on a sidewall of the outer body.

7. The click and release controlled endoscopic needle as in claim 1 wherein the internal stop includes an open central portion.

8. The click and release controlled endoscopic needle as in claim 1 wherein said plunger includes a hollow interior.

9. The click and release controlled endoscopic needle as in claim 8 wherein the hollow needle is secured within the hollow interior of the plunger.

10. The click and release controlled endoscopic needle as in claim 8 wherein the hollow needle is positioned so that the hollow interior of the hollow needle opens into the hollow interior of the plunger.

11. The click and release controlled endoscopic needle as in claim 1 wherein the flexible member further includes a handle and flexes along a rear portion.

12. The click and release controlled endoscopic needle as in claim 1 wherein the flexible member has a shaped proximal opening through which the distally extending projection is insertable.

13. The click and release controlled endoscopic needle as in claim 1 further including an end cap removably connected to the proximal end of the plunger and a stylet connected to the cap and passing through the hollow needle to the distal end thereof.

14. The click and release controlled endoscopic needle as in claim 1 wherein the flexible member includes a pair of side edges and a rear connecting hinge.

15. A click and release controlled endoscopic needle for collecting tissue, cell and/or fluid specimens from a patient comprising:

a controller comprising an outer body having a hollow interior and proximal and distal ends, an internal stop, a plunger also having proximal and distal ends with at least a portion of the plunger being slidable within the outer body, and a spring interposed within the hollow interior between the internal stop and the plunger distal end;

a click and release mechanism operatively interposed between the plunger and the outer body to control the relative sliding positions there between, the click and release mechanism comprising a movable member at the proximal end of the outer body including a pawl, the plunger having a first portion slidable within the outer body, and a distally extending second portion spaced away from the first portion and located at an intermediate position between the proximal and distal ends of the plunger so that the second portion can interact with the movable member, the second portion having a plurality of spaced apart teeth formed thereon for releasably engaging the pawl to hold the plunger in a pushed-in position against the force of the spring when one of the plurality of teeth engages the pawl, at least two of the plurality of teeth being spaced apart by a distance defining a toothless surface there between to permit the plunger to be pulsed axially along said toothless surface, and a handle member located adjacent the proximal end of the of the plunger;

a hollow needle having proximal and distal ends, the proximal end attached to the plunger; and a flexible outer tube attached to the controller and extending along the length of the hollow needle.

16. The click and release controlled endoscopic needle as in claim 15 wherein the second portion extends parallel to the first portion.

17. The click and release controlled endoscopic needle as in claim 15 wherein the movable member includes a shaped opening including the pawl at a proximal end for receiving the second portion therein.

18. The click and release controlled endoscopic needle as in claim 15 wherein movement of the movable member toward the interior of the outer body releases the pawl from the plurality of spaced apart teeth allowing the spring force to push the plunger proximally.

* * * * *